United States Patent
Liu

(10) Patent No.: US 10,058,512 B2
(45) Date of Patent: Aug. 28, 2018

(54) RUMEN PROTECTED GLUCOSE AND METHOD OF PREPARATION

(71) Applicant: Chunhai Liu, Beijing (CN)

(72) Inventor: Chunhai Liu, Beijing (CN)

( * ) Notice: Subject to any disclaimer, the term of this patent is extended or adjusted under 35 U.S.C. 154(b) by 2 days.

(21) Appl. No.: 15/590,799

(22) Filed: May 9, 2017

(65) Prior Publication Data

US 2018/0169026 A1    Jun. 21, 2018

(30) Foreign Application Priority Data

Dec. 16, 2016   (CN) .......................... 2016 1 1170409

(51) Int. Cl.
*A61K 9/50* (2006.01)
*A23K 40/35* (2016.01)
*A61K 9/20* (2006.01)

(52) U.S. Cl.
CPC ............ *A61K 9/5084* (2013.01); *A23K 40/35* (2016.05); *A61K 9/2081* (2013.01)

(58) Field of Classification Search
CPC .................................................. A61K 9/5084
See application file for complete search history.

(56) References Cited

U.S. PATENT DOCUMENTS 8,110,214 B2   2/2012   Porter et al.
9,511,062 B2   12/2016  Garrett et al.

FOREIGN PATENT DOCUMENTS

| CN | 101543471 A | 9/2009 |
| CN | 101664108 A | 3/2010 |
| CN | 202218585 U | 5/2012 |

OTHER PUBLICATIONS

Gruffat D.,Durand D,Graulet B. Regulation of VLDL synthesis and secretion in the liver. Reproduction Nutrition Development, 1996, 36(4):375-389.

Goff, J.P., and R.L.Horst. Physiological changes at parturition and their relationship to metabolic disorders. J. Dairy Sci.1997b 80:1260-1268.

Hocquette, J.F.,and D.Bauchart. Intestinal absorption ,blood transport,and hepatic muscle metabolism of fatty acids in preruminant and ruminant animals.1999 Reprod.Nur.Dev.39:27-48.

孙斌, 赵凯, 王洪, 奶牛酮病及其研究进展, 黑龙江八一农垦大学学报, 1999, 11(3):485-51. Sun B, Zhao K, Wang H, Research Progress of Ketosis in Dairy Cow. HeiLongJiang Ba Yi University, J of Agricultural Reclamation. 1999, 11(3): 48-51.

*Primary Examiner* — David J Blanchard
*Assistant Examiner* — Daniel F. Coughlin
(74) *Attorney, Agent, or Firm* — Jeanette Meng Nakagawa

(57) ABSTRACT

The present disclosure provides a preparation method of rumen protected glucose, comprising the following steps: (1) preparing glucose into a pellet and drying; (2) fluidizing the pellet in a fluidized bed after drying; and (3) coating melted aliphatic alcohol and/or saturated fatty acid onto the surface of the pellet located in the fluidized bed to obtain a rumen protected bypass glucose particle. The prepared rumen-protected glucose could go through the rumen of ruminant effectively; and the availability of coating layer in ruminant increases, making the coated glucose be released completely and fully utilized by ruminant, so ketosis or subclinical ketosis and fatty liver disease of the ruminants in perinatal stage could be prevented and reduced effectively, the postpartum weight loss could be reduced, and the cycle conception rate and the milk yield could be increased.

9 Claims, No Drawings

RUMEN PROTECTED GLUCOSE AND METHOD OF PREPARATION

CROSS REFERENCE TO RELATED APPLICATION

The Present application claims priority through Paris Convention to a Chinese Patent Application No. 201611170409.3, filed on Dec. 16, 2016, which is hereby incorporated herein by reference in its entirety.

TECHNICAL FIELD

The present disclosure relates to the field of preparing ruminant nutrient substance, more specifically to a preparation method of rumen protected glucose.

BACKGROUND

Rumen is the first stomach of ruminants. 75-80% dry matter, as well as above 50% crude fiber in daily ration that ingested by a cow is digested in the rumen. By specific process of the rumen bypass technology, certain nutrient substances (such as protein, amino acid and vitamin etc.) could be protected, the fermentation and degradation thereof in rumen of the ruminants could be reduced, and these nutrient substances could go directly into small intestine and then be digested and absorbed, so as to improve the efficiency of feed utilization.

After calving, the milk yield of the cow will increase rapidly, so the demand of the cow for energy, especially for glucose will increase, however, carbohydrate provided by the daily ration for synthesizing glucose is far from enough, which will cause the decrease of blood glucose, further cause the starting of gluconeogenesis mechanism, the employ of body protein, the steatolysis of the body fat, and finally cause the happening of ketosis or subclinical ketosis and fatty liver disease.

The ketosis is an energy metabolic disorder disease that is caused by dairy cow's metabolic disorder of saccharides and fat and characterized in hypoglycemia, and the cow's metabolic disorder of saccharides and fat leads to the accumulation of a lot of ketone body (including β-hydroxybutyrate (BHBA), acetoacetic acid and acetone, mainly β-hydroxybutyrate) in blood, and the ketone body excretes in urine, milk and exhaled gases. (SUN Bin, etc., 1999; Gruffat D. et al, 1996; Goff J P and Horst R L, 1997; Hocquette J F and Bauchart D, 1999). The disease is common and severe nutrition metabolic disease for dairy cow, and mostly happens in the 10-60 days after calving. Although ketosis could be cured, it will cause multiple diseases such as the decline in milk yield, milk quality and reproductive rate, as well as the reproductive system disease and endocrine disorder, and these diseases increase the treatment costs, and cause serious economic loss.

Fatty liver disease is a secondary phenomenon of ketosis, and a nutrition metabolic disease. Due to the imbalance of glycometabolism of cow in perinatal stage, a lot of free fatty acids (non-esterified fatty acid) are produced by the lipolysis of body fat, and these free fatty acids are transported to the liver, while it does not have enough time for these free fatty acids to be transported to other tissues or to be oxidized, so free fatty acid accumulation happens in liver which causes fatty liver disease.

At present, ketosis of dairy cow is generally treated by intravenous injection of glucose, which is usually administrated for 5 days. This treatment is not only easy to cause the stress in cow, but also inconvenient for the operation. Furthermore, there is no effective method to prevent this disease. Because the glucose added directly into daily ration will be destroyed by rumen microorganism in rumen, and cannot go through rumen effectively, the method of introducing the glucose into the daily ration cannot prevent the ketosis in dairy cow.

The rumen bypass protection technology (rumen bypass technology for short) could alleviate the above ketosis or the subclinical ketosis and the fatty liver disease, specifically, it could prevent the nutrient substances which can be easily destroyed by rumen microorganism from disassembling by rumen microorganism by utilizing physical or chemical means, it also could form a coating layer on the surface of the nutrient substances that can be easily destroyed by rumen microorganism, and the nutrient substances could be re-released in abomasum and intestinal tract and utilized by ruminant, so the body requirement for glucose can be met and unnecessary sugar dysplasia mechanism can be avoided.

However, the rumen bypass protection technology in the prior art still has the following disadvantages: 1. the glucose which needs to be protected is not coated completely, so it can be easily degraded by rumen microorganism and the rumen bypass ratio is low; 2. the coating layer is lowly utilized by ruminant, hence, the coated glucose cannot be released completely and cannot be fully utilized by ruminant.

The information disclosed in this Background of the Invention section is only for enhancement of understanding of the general background of the invention and should not be taken as an acknowledgement or any form of suggestion that this information forms the prior art already known to a person skilled in the art.

SUMMARY OF THE INVENTION

The object of this disclosure is to provide a preparation method of rumen protected glucose. In this method, glucose could be coated completely so the rumen protected glucose could bypass the rumen of ruminant effectively; and the availability of coating layer in ruminant increases, making the coated glucose be released completely and fully utilized by ruminant, so ketosis or subclinical ketosis and fatty liver disease of the ruminants in perinatal stage could be prevented and reduced effectively, the postpartum weight loss could be reduced, and the cycle conception rate and the milk yield could be increased.

To achieve the above objective, the disclosure provides a preparation method of rumen protected glucose, comprising the following steps:

(1) preparing glucose into a pellet and drying;
(2) fluidizing the pellet in a fluidized bed after drying; and
(3) coating melted aliphatic alcohol and/or saturated fatty acid onto the surface of the pellet located in the fluidized bed to obtain a rumen protected bypass glucose particle.

The disclosure further provides a preparation method of rumen protected glucose, wherein the glucose can be replaced by either disaccharide, or polysaccharide, or a combination of both. Disaccharide may comprise: saccharose, maltose, and lactose etc., with an exception of brown sugar. Polysaccharide may comprise various starches.

Preferably, in the above technical solution, the ratio by weight range of the glucose to aliphatic alcohols, or saturated fatty acids, or a combination thereof, is 25-75:45-70.

Preferably, in the above technical solution, the ratio by weight of the glucose to aliphatic alcohol and/or saturated fatty acid is 25-53:45-70.

Preferably, in the above technical solution, before preparing the glucose into a pellet, the preparation method of rumen protected bypass glucose further includes the step of mixing the glucose with lipase, and the lipase is the high temperature resistant lipase. The enzyme activity of the used high temperature resistant lipase is not less than 10000 U/g, and the used high temperature resistant lipase is tolerant for high temperature, the enzyme activity of which could maintain above 85% at the temperature of 85° C. and maintain a high level at pH 3-11.

Preferably, in the above technical solution, each of 1 g glucose needs to be added 0.01 U-0.2 U lipase.

Preferably, in the above technical solution, the melting point of the saturated fatty acid is above 52° C., and the percentage by weight of C16~C18 saturated fatty acid of the saturated fatty acid is above 70%, which includes stearic acid and hydrogenated fatty acid of animals and plants. The saturated fatty acid is commercially available, or the saturated fatty acid could be prepared from the unsaturated fatty acid by a person skilled in this art through the prior techniques.

Preferably, in the above technical solution, the aliphatic alcohol and/or saturated fatty acid contain a pH sensitive material, wherein the pH sensitive material does not dissolve in water at pH 6-7, while dissolves in water below pH2-3, such as chitosan and polyacrylate IV etc.

Preferably, in the above technical solution, the ratio by weight range of the pH sensitive material to glucose is 1-5:25-75.

Compared with the related art, the present disclosure has the following beneficial technical effects: 1. through the coating method of the present disclosure, the content of the coated glucose in glucose pellets increases, the glucose is coated completely, and there is no residue of glucose particles in coating layer, so the rumen bypass percentage of glucose increases at least 25%-40%, which increases greatly to above 90%, and the requisite amount of ruminant for glucose during lactation period could be better satisfied; 2. the mixture which includes glucose also contains lipase, making the fatty acid be decomposed rapidly under the existence of gastric acid after the glucose pellet goes into the abomasum, which further makes the coated glucose be released more effectively, and the release rate thereof in small intestine could achieve 90%.

Furthermore, through the above rumen bypass protection technology, the rumen protected bypass glucose could go through the rumen of the ruminant more effectively, and block the sugar dysplasia mechanism caused by the sugar metabolism imbalance of the ruminants in perinatal stage, so as to prevent the body protein from being employed, the body fat from being degraded and plenty of free fatty acid from being generated. The rumen protected bypass glucose is not only able to prevent effectively the happening of subclinical ketosis, clinical ketosis and fatty liver disease, but also able to treat the ketosis directly. Furthermore, the rumen protected bypass glucose is able to reduce the happening of postpartum weight loss and to increase the cycle conception rate. Moreover, the rumen protected bypass glucose can be offered to the ruminant directly, which offers energy to the ruminant, making a balance among the rumen bypass glucose, the rumen bypass fat and the rumen bypass amino acid and an increased milk yield, which is also meaningful for the health of ruminant.

DETAILED DESCRIPTION OF THE EMBODIMENTS

The present disclosure has been described using detailed descriptions of embodiments thereof that are provided by way of example and are not intended to limit the scope of the invention.

The high temperature resistant lipase with an enzyme activity of 10000 U/g used in the following embodiments is provided by AsiaPac Bio-Technology Co., Ltd, the enzyme activity thereof could maintain above 85% at the temperature of 85° C. and maintain a high level at pH 3-11.

The melting point of the saturated fatty acid used in the following embodiments is above 52° C., and the percentage by weight of C16~C18 saturated fatty acid in the saturated fatty acid is 70%.

Example 1, 30% Rumen Protected Glucose was Prepared 30.5 kg of glucose was weighed and smashed to pass through 120 mesh sieve; meanwhile, 200 mg of high temperature resistant lipase with the enzyme activity of 10000 U/g was weighed and mixed into the glucose; then 8 kg of water was added to obtain the moist material; furthermore, the moist material was extruded with extruder and shot blasting was processed; and then drying was proceeded at a low temperature below 60° C. to obtain the glucose pellet.

65.5 kg of saturated fatty acid and 4 kg of chitosan were heated to 120° C. to obtain melts.

The glucose pellet was fluidized in a fluidized bed of bottom spray coating machine, and the melts which were cooled to below 100° C. were sprayed onto the surface of the glucose pellet, then the rumen protected bypass glucose with 30% glucose was made.

Example 2, 50% Rumen Protected Glucose was Prepared 50.5 kg of glucose was weighed and smashed to pass through 120 mesh sieve; meanwhile, 400 mg of high temperature resistant lipase with the enzyme activity of 10000 U/g was weighed and mixed into the glucose; then 13 kg of water was added to obtain the moist material; furthermore, the moist material was extruded with extruder and shot blasting was processed; and then drying was proceeded at a low temperature below 60° C. to obtain the glucose pellet.

47.5 kg of saturated fatty acid and 2 kg of polyacrylic resin IV were heated to 120° C. to obtain melts.

The glucose pellet was fluidized in a fluidized bed of bottom spray coating machine, and the melts which were cooled to below 100° C. were sprayed onto the surface of the glucose pellet, then the rumen protected bypass glucose with 50% glucose was made.

Comparative Example, 45% Rumen Protected Glucose was Prepared 45.5 g of glucose was weighed and smashed to pass through 120 mesh sieve; 51 g of saturated fatty acid and 4 g of nylon were weighed and heated to 160° C. to obtain melts; the glucose was added into the melts which were cooled to 100° C., the mixture was formed after even stirring, then the mixture was added into high pressure sprayer, sprayed into the fluidized bed with 20° C. cool air and cooled, then the rumen bypass glucose with 45% glucose was made.

Example 3 Example of Effects

In order to testify the properties of the rumen bypass glucose, in vitro method was employed to simulate the digestive tract of the ruminant to proceed the stability test (the simulated rumen environment: buffer solution of pH 6.6 and 5.4, the simulated abomasum and duodenum environment: buffer solution of pH 2.4) and evaluation.

Materials and Methods

The buffer solutions of pH 6.6, 5.4 and 2.4 were employed in the study to simulate the ruminant's rumen, abomasum and duodenal gastrointestinal tract respectively.

Formulation of Buffer Solutions of Different pH

TABLE 1

Formulation of buffer solutions of different pH (g)

| Reagent | pH 6.6 | pH 5.4 | pH 2.4 |
|---|---|---|---|
| Citric acid ($C_6H_8O_7 \cdot H_2O$) | 5.7225 | 9.297 | 19.698 |
| Sodium hydrogen phosphate ($Na_2HPO_4 \cdot 12H_2O$) | 52.089 | 39.936 | 4.4392 |

(1) The substances listed in the table are dissolved in a small amount of distilled water, and adjusted to 1000 mL.

Test Samples

Sample A: the rumen bypass glucose prepared in Example 1, the content of glucose: 30%;

Sample B: the rumen bypass glucose prepared in Example 2, the content of glucose: 50%;

Sample C: the rumen bypass glucose prepared in comparative example, the content of glucose: 45%;

Three production batches for each sample, each 400 g, reserved;

Stability Test for Rumen Protected Glucose at Buffer Solutions of Different pH 1.0000 g of samples A, B and C were accurately weighed and respectively added into the bottom of a 50 mL test tube with a stopper, 20 mL of buffer solution was respectively added in, then the test tubes were fastened with tube stoppers and digested in thermostatic shaking water bath of 39° C. for 2, 4, 8, 12 and 24 h. Samples A, B and C were washed after the test tubes were taken out and the buffer solutions were filtered, and the filter liquor was adjusted, then the content of the glucose in the filter liquor was measured. Based on the content of the glucose in the filter liquor, the rumen bypass percentage and the releasing percentage in small intestine of glucose were calculated. Each coated rumen bypass glucose sample was set three repetitions at each point in time.

Test method of glucose: GB/T22221, a high performance liquid chromatography method of measuring the fructose, glucose, sugar, maltose and lactose in food.

Computational Formula

Rumen bypass percentage of product($W1$)=(1−$A2$)/$A1$×100%

In Formulation: A1—the content of glucose in product; A2—the content of glucose in filter liquor of buffer solution of pH6.6.

The releasing percentage of product in small intestine ($W2$)=$A3$/$A1$×100%

In Formulation: A1—the content of glucose in product; A3—the content of glucose in filter liquor of buffer solution of pH2.4.

The effective releasing percentage of product=$W1$×$W2$×100%

In Formulation: W1—the rumen bypass percentage of product;

W2—the releasing percentage of product in small intestine.

Statistical Approach

SPSS 19.0 was used in statistical analysis.

Result Analysis

The Rumen Bypass Percentage of Each Product at Different Point-in-Time (pH6.6)

It can be seen from Table 1 that, the rumen bypass percentage of each test sample is Sample A=Sample B>Sample C, wherein each test sample was cultivated in buffer solution of pH6.6 under the condition of 39° C. constant temperature bath.

TABLE 1

The rumen bypass percentage of each product at different point-in-time(%)

| Time | 2 h | 4 h | 8 h | 12 h | 24 h |
|---|---|---|---|---|---|
| Sample A | 96.40 | 93.51 | 80.50 | 73.00 | 69.50 |
| Sample B | 96.80 | 93.10 | 79.10 | 72.15 | 70.21 |
| Sample C | 82.00 | 72.00 | 64.90 | 58.20 | 50.20 |

The Releasing Percentage of Each Product in Small Intestine at Different Point-in-Time (pH2.4)

It can be seen from Table 2 that, the releasing percentage in small intestine of each test sample is Sample A=Sample B>Sample C, wherein each test sample was cultivated in buffer solution of pH2.4 under the condition of 39° C. constant temperature bath.

TABLE 2

The release rate of product in small intestine of each product at different point-in-time(%)

| Time | 2 h | 4 h | 8 h | 12 h | 24 h |
|---|---|---|---|---|---|
| Sample A | 92.20 | 97.30 | 100.00 | 100.00 | 100.00 |
| Sample B | 93.14 | 97.80 | 100.00 | 100.00 | 100.00 |
| Sample C | 89.00 | 92.00 | 94.50 | 95.30 | 97.40 |

The Effective Releasing Percentage of Each Product at Different Point-in-Time

It can be seen from Table 3 that, the effective releasing percentage of each test sample is Sample A=Sample B>Sample C, wherein each test sample was cultivated in buffer solution of pH6.6 and pH2.4 under the condition of 39° C. constant temperature bath.

TABLE 3

The effective releasing percentage of each product at different point-in-time (%)

| Time | 2 h | 4 h | 8 h | 12 h | 24 h |
|---|---|---|---|---|---|
| Sample A | 88.9 | 91.0 | 80.5 | 73.0 | 69.5 |
| Sample B | 90.2 | 91.1 | 79.1 | 72.2 | 70.2 |
| Sample C | 73.0 | 66.2 | 61.3 | 55.5 | 48.9 |

CONCLUSION

Several rumen protected glucose products were cultured in vitro, and the rumen bypass percentage, the releasing percentage in small intestine and the effective releasing percentage of each product at different point-in-time were obtained by simulating ruminant rumen fluid and the small intestine fluid. The experiment results show the rumen bypass percentage, the releasing percentage in small intestine and the effective releasing percentage of the rumen bypass glucose of the products in the present disclosure have been significantly improved compared with those of product obtained in comparative example. The similar experiment effect could also be obtained when the weight percentage of C16~C18 saturated fatty acid in the saturated fatty acid used in the preparation of samples A, B and C is more than 70%.

The foregoing descriptions of specific embodiments of the present invention are presented for purposes of illustration and description. It is not intended to be exhaustive or to limit the invention to the precise form disclosed, and obviously many modifications and variations are possible in light of the above teaching. The exemplary embodiments were chosen and described in order to explain certain principles of the invention and their practical application, to thereby enable others skilled in the art to make and utilize various exemplary embodiments of the present invention, as well as various alternatives and modifications thereof. The invention is to be limited only by the claims provided below and equivalents thereof.

What is claimed is:

1. A method of preparing rumen protected glucose, comprising:
    mixing glucose and lipase, wherein the lipase is heat tolerant and comprises an enzyme activity of no less than 10,000 U/g, with the enzyme activity maintained no less than 85% at a temperature of 85° C., with a pH range of 3-11;
    rendering and drying the glucose/lipase mixture into glucose/lipase pellets;
    fluidizing the glucose/lipase pellets in a fluidized bed after drying; and
    coating all surfaces of the glucose/lipase pellets with melted aliphatic alcohols and/or saturated fatty acids in the fluidized bed.

2. A method of preparing rumen protected disaccharide and/or polysaccharide, comprising:
    mixing a disaccharide and/or a polysaccharide and lipase, wherein the lipase is heat tolerant and comprises an enzyme activity of no less than 10,000 U/g, with the enzyme activity maintained no less than 85% at a temperature of 85° C., with a pH range of 3-11;
    rendering and drying the disaccharide and/or polysaccharide/lipase mixture into disaccharide and/or polysaccharide/lipase pellets;
    fluidizing the disaccharide and/or polysaccharide/lipase pellets in a fluidized bed after drying; and
    coating all surfaces of the disaccharide and/or polysaccharide/lipase pellets with melted aliphatic alcohols and/or saturated fatty acids in the fluidized bed.

3. The method of preparing rumen protected glucose of claim 1, wherein the weight range of the glucose is 25 to 75%.

4. The method of preparing rumen protected glucose of claim 1 wherein the step of mixing the glucose and the lipase comprises mixing the lipase and the glucose at a ratio of 0.01 U-0.2 U of lipase per gram of glucose.

5. The method of preparing rumen protected glucose of claim 1, wherein the melting point of the saturated fatty acids is above 52° C., and wherein the saturated fatty acids comprise greater than 70% wgt of $C_{16}$-$C_{18}$ saturated fatty acids.

6. The method of preparing rumen protected disaccharide and/or polysaccharide of claim 2, wherein the weight range of the disaccharide and/or polysaccharide is 25%-75%.

7. The method of preparing rumen protected disaccharide and/or polysaccharide of claim 2, wherein the step of mixing disaccharide and/or polysaccharide with lipase comprises mixing the disaccharide and/or polysaccharide and the lipase at a ratio of 0.01 U-0.2 U of lipase per gram of disaccharide and/or polysaccharide.

8. The method of preparing rumen protected disaccharide and/or polysaccharide of claim 2, wherein the melting point of the saturated fatty acids is above 52° C., and wherein the saturated fatty acids comprise greater than 70% wgt of $C_{16}$-$C_{18}$ saturated fatty acids.

9. A method of preparing rumen protected glucose, comprising:
    mixing glucose and lipase, wherein the lipase is heat tolerant and comprises an enzyme activity of no less than 10,000 U/g, with the enzyme activity maintained no less than 85% at a temperature of 85° C., with a pH range of 3-11;
    rendering and drying the glucose/lipase mixture into glucose/lipase pellets;
    fluidizing the glucose/lipase pellets in a fluidized bed after drying; and
    coating all surfaces of the glucose/lipase pellets with melted aliphatic alcohols and/or saturated fatty acids in the fluidized bed to obtain a rumen protected glucose pellets, with a weight range of the glucose of 25%-75%.

* * * * *